United States Patent [19]

Butelman

[11] Patent Number: 5,021,561

[45] Date of Patent: Jun. 4, 1991

[54] COMPLEXES OF IRON OR OTHER METALS WITH SULPHONATED DERIVATIVES OF CHITOSAN

[75] Inventor: Federico Butelman, Milan, Italy

[73] Assignee: Etablissement Texcontor, Vaduz, Liechtenstein

[21] Appl. No.: 438,077

[22] Filed: Nov. 20, 1989

[30] Foreign Application Priority Data

Apr. 10, 1989 [IT] Italy ................... 20082 A/89

[51] Int. Cl.$^5$ .................. C08B 37/00; C07H 5/00; C07H 11/00; C07H 1/00; A61K 31/00
[52] U.S. Cl. ................... 536/20; 536/17.2; 536/17.5; 536/17.6; 536/17.9; 536/18.7; 536/22; 536/43; 536/54
[58] Field of Search ............ 536/20, 121, 124, 17.2, 536/17.5, 17.6, 17.9, 18.7, 22, 43, 54; 514/55

[56] References Cited

U.S. PATENT DOCUMENTS

| | | | |
|---|---|---|---|
| 4,125,708 | 11/1978 | Masri et al. ............... | 536/20 |
| 4,301,067 | 11/1981 | Koshugi ................... | 536/20 |
| 4,810,695 | 3/1989 | Conti et al. ............... | 536/20 |

FOREIGN PATENT DOCUMENTS 3432227  3/1986  Fed. Rep. of Germany ........ 536/20

Primary Examiner—Ronald W. Griffin
Assistant Examiner—Everett White
Attorney, Agent, or Firm—Birch, Stewart, Kolasch & Birch

[57] ABSTRACT

Complexes of iron or other metals with sulphonated derivatives of chitosan, having the following general formula (I):

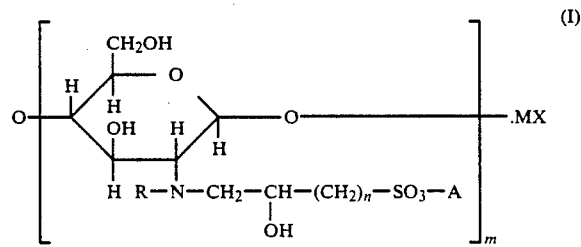

in which:
R is H or a $C_1$-$C_5$ alkyl group, or an arylalkyl group;
A is H or an alkaline metal or an alkaline earth metal;
X is a pharmacologically acceptable anion;
m is a whole number from 50 to 1000;
n is zero or a whole number from 1 to 10;
M is $Fe^{II}$, $Fe^{III}$, Mg, Ca or Bi.

9 Claims, No Drawings

COMPLEXES OF IRON OR OTHER METALS WITH SULPHONATED DERIVATIVES OF CHITOSAN

FIELD OF THE INVENTION

This invention relates to water-soluble metal complexes with sulphonated derivatives of chitosan. When said complexes are of iron, they can be used in therapy for the treatment of sideropenia.

PRIOR ART

Chitosan is a polysaccharide obtained by deacetylating chitin by treatment with strong bases.

Chitin itself is a widely distributed natural polysaccharide consisting essentially of units of N-acetyl-D-glucosamine, which is extracted from crab shells.

Chitosan is used industrially, for example in water treatment, in the preparation of photographic emulsions and in improving the dyeing of synthetic and natural fibres.

In the pharmaceutical field chitosan is used in the preparation of cicatrizants.

SUMMARY OF THE INVENTION

We have now discovered new compounds consisting of complexes of $Fe^{II}$, $Fe^{III}$ or other metals with sulphonated derivatives of chitosan. The $Fe^{II}$ or $Fe^{III}$ complexes can be used in solution form in the treatment of sideropenia.

Said complexes have the following general formula (I):

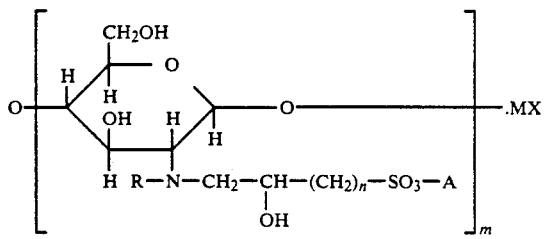

in which:
R is H or a $C_1$-$C_5$ alkyl group or an arylalkyl group;
A is H or an alkaline metal or an alkaline earth metal;
X is a pharmacologically acceptable anion;
m is a whole number from 50 to 1000;
n is zero or a whole number from 1 to 10;
M is $Fe^{II}$, $Fe^{III}$, Mg. Ca or Bi. Said complexes are prepared by:

a) hydrolyzing-activating commercial chitosan by treatment with an organic acid, possibly mixed with an alkaline nitrite, and later with alkaline hydroxyde;

b) functionalizing by treatment in an organic solvent or in water or in a mixed organic-aqueous solvent with a chlorohydrin or epoxy compound carrying a sulphonated group at one end of its chain;

c) treating with a $Fe^{II}$ and/or $Fe^{III}$ or Mg or Ca or Bi salt in aqueous solution and precipitating the complex by adding a water-soluble organic solvent;

d) neutralizing the sulphonic group with an alkaline or alkaline-earth hydroxide or other strong base in aqueous and/or organic or mixed organic/aqueous solution and precipitating the neutralized complex by adding a water-soluble organic solvent if operating in an aqueous environment, or recovering the neutralized complex by filtration if operating in an organic solvent or mixed organic/aqueous solvent.

DETAILED DESCRIPTION OF THE INVENTION

The characteristics and advantages of the complexes of $Fe^{II}$, $Fe^{III}$, Mg, Ca or Bi with sulphonated derivatives of chitosan and of their preparation method according to the present invention will become apparent during the course of the following detailed description. The complexes according to the invention are prepared by a method which uses commercial chitosan as starting material. This product is not suitable for the direct preparation of soluble complexes according to the invention because of its too high molecular weight ($>1,000,000$) and its low surface area, which limits its reactivity.

To overcome this drawback, the commercial chitosan is subjected to hydrolyzing-activating pretreatment.

This pretreatment is effected by adding to the chitosan an organic acid such as a 0.1M solution of acetic acid or formic acid, heating under reflux for 20–30 hours and then precipitating the hydrolyzed product by adding 5N NaOH.

Alternatively 0.4–0.5M commercial acetic acid and sodium nitrite can be added to the commercial chitosan and the mixture stirred at ambient temperature for 15-20 hours. The hydrolyzed product is again precipitated with 5N NaOH.

This pretreatment results in chitosan having a molecular weight and morphology which make it much more reactive than the starting substance and suitable for preparing soluble complexes.

The chitosan formed in this manner is functionalized by treatment with a chlorohydrin or epoxy compound comprising from two to twelve carbon atoms and carrying a sulphonated group at one end of the hydrocarbon chain as indicated by the structures (II) and (III):

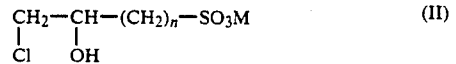

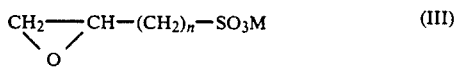

where n is zero or a whole number from 1 to 10, and M is H or an alkaline or alkaline-earth metal.

This treatment is conducted in an organic solvent or in water or in a mixed organic/aqueous solvent.

Organic solvents which can be used include ethylene glycol, methanol and higher linear or branched homologous alcohols up to 7 carbon atoms, either alone or in mixture with each other.

Aprotic dipolar solvents can also be used, such as N,N-dimethyformamide, N,N-dimethyacetamide and dimethysulphobxide.

The molar ratio of chitosan to be chlorohydribn or epoxy compound can vary from 1:0.5 to 1:6 depending on the degree of substitition and solubility required.

The treatment is conducted at a temperature of between 60° C. and 120° C. for a time of between 6 and 16 hours.

In this manner a compound is obtained of general formula (IV):

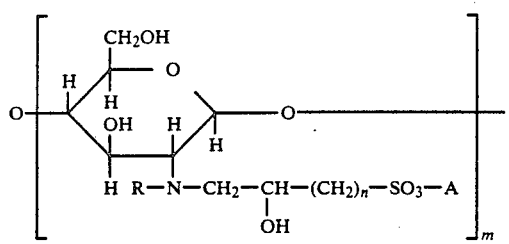

(IV)

which is a new compound. usable for the subsequent reactions and possibly for other uses.

An alkyl or arylalkyl group is introduced into the secondary amino group of (IV) by conventional N-alkylation methods.

Preparation of the Metal Complex

The compound (IV). possibly alkylated in the aforesaid manner, is dissolved in water in such a quantity as to obtain a concentration of between 8% and 13% w/v.

An $Fe^{II}$, $Fe^{III}$, Mg, Ca or Bi salt is added to this solution in a quantity such as to obtain a compound (IV) monomer unit to metal ion molar ratio of between 1:1 and 1:1.5 and operating at acid pH such as to keep said salt in solution. Said salt is a sulphate, nitrate, acetate or chloride.

The mixture is kept at a temperature of between 10° C. and 25° C., under stirring, for 15-20 hours and the reaction product is recovered by precipitation by adding a volume of organic solvent equal to 8 times the volume of the reaction mixture. Suitable solvents are acetone, methanol, isopropanol or other water-miscible solvents.

The solid product obtained is filtered off, washed with ethyl ether and dried under vacuum.

In this manner the metal ion complex of formula (V) is obtained:

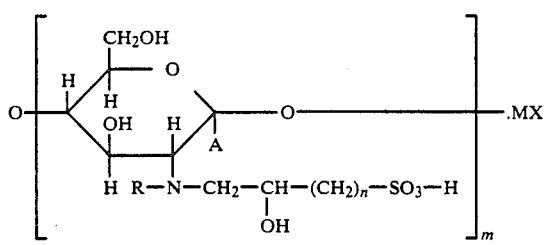

(V)

The compound (V) is suspended in water or in a suitable organic or aqueous/organic system in a quantity of between 8% and 13% w/v and added at ambient temperature to the stoichiometric quantity of alkaline or alkaline-earth hydroxide or another strong base to neutralize the sulphonic group. The pH must exceed 7.5.

The final compound (I) is precipitated from the obtained solution by adding an organic solvent in a quantity of 8 times the solution volume.

The solvent used can be acetone, methanol, isopropanol or another water-miscible solvent. If the system is organic the compound (I) is recovered by filtration.

The compound (I) is washed with ethyl ether and dried under vacuum.

The compound (I) has high water solubility and high stability in aqueous solution.

If (I) is the $Fe^{II}$ or $Fe^{III}$ complex it can be used in solution form in therapy to compensate for iron deficiency.

The release of iron into the intestinal tract occurs gradually, the polymer part not being absorbed and not giving rise to any side effect.

The following examples of the preparation of complexes according to the invention are given for non-limiting illustrative purposes only.

EXAMPLE 1

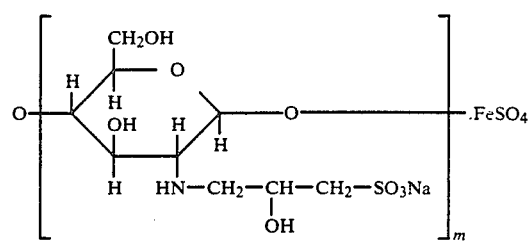

20.0 g of commercial chitosan with an 80% degree of deacetylation, equivalent to 0.12 moles, are hydrolyzed by treatment with 1.0 liters of 0.1N HCOOH under reflux for 24 h.

The hydrolysis product is precipitated with 5N NaOH and then washed with isopropanol until a water content of 15% is determined by the Karl Fischer method. 18.0 g of hydrolyzed product are obtained. 46.3 grams of sodium 3-chloro-2-hydroxypropyl sulphonate (0.24 moles) are dissolved in 40.0 ml of water, after which 8.5 g (0.212 moles) of solid NaOH are added. The mixture is stirred for 6 h after which 130 ml of isopropanol and the 18.0 g of chitosan from the previous stage are added. The mixture is heated under reflux for 8 h after which it is filtered while hot. The solid obtained is washed 3 times with a methanol/water (10/3)mixture, using 150 ml each time, and once with 100 ml of methanol.

32.5 g of a white solid are obtained which on microanalysis is shown to have an S content of 8.0% and a sodium content of 5.7%.

The 32.5 g of functionalized product (0.11 moles) are dissolved in 320 ml of water and 60.7 g (0.22 moles) of $FeSO_4.7H_2O$ are added.

After 16 hours at 25° C. the product is precipitated by adding acetone in a quantity of 2600 ml. filtered off, washed with ethyl ether and dried. 36 g of product are obtained having an $Fe^{II}$ content of 15.0%.

This solid is suspended in 360 ml of water and 4.4 g (0.11 moles) of solid NaOH are then added to mixture. The obtained product is recovered by precipitation by adding acetone in the manner of the previous step. 37.0 g of water-soluble product are obtained, a 5% w/v solution of which has a pH of about 8.0 and which has an $Fe^{II}$ content of 12%.

EXAMPLE 2

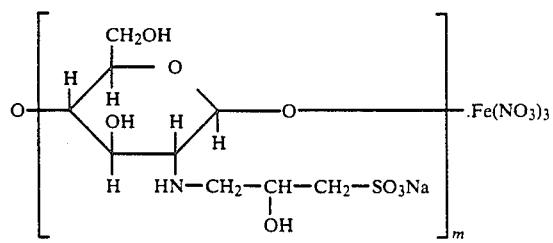

30.0 g of 2[N(sodium 2-hydroxypropyl sulphonate)] poly-D-glucosamine (0.10 moles), prepared as in Example 1, are suspended in 300 ml of methanol and 90 ml of water.

40.4 g of Fe(NO$_3$)$_3$.9H$_2$O (0.1 moles) are added to this suspension under stirring. Stirring is continued for 16 hours at a temperature of 25° C. The solid is then filtered off and washed 3 times with 100 ml of methanol until uncomplexed Fe$^{III}$ is eliminated. 38.0 g of a yellow solid product are obtained containing 12.5% of Fe$^{III}$. It is then treated with NaOH as specified in Example 1.

In this manner 42.0 g of product are obtained with an Fe$^{III}$ content of 10.5%

EXAMPLE 3

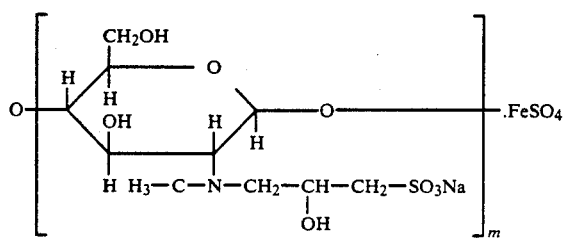

30.0 g of 2-[N-(sodium 2-hydroxypropyl sulphonate)] poly-D-glucosamine (0.10 moles) are suspended in 300 ml of isopropanol. 20.5 ml of a 40% w/v solution of formic aldehyde (0.2730 moles) and 17.0 g of 98% formic acid (0.364 moles) are then added to this suspension in the stated order. It is heated under reflux until CO$_2$ evolvement ceases. The suspension is then filtered and the solid washed with a little isopropanol. In this manner 30.5 g of water-soluble product are obtained.

The solid obtained is dissolved in 305 ml of distilled water. 49.3 g of FeSO$_4$.7H$_2$O (0.18 moles) are added to this solution, which is then left stirring at 25° C. for 16 hours.

31.5 g of product are obtained containing 13.5% of Fe$^{II}$. This quantity is suspended in 315.0 ml of distilled water containing 3.5 g of NaOH (0.088 moles) and the suspension left stirring for 1 hour at 25° C. The solid product is recovered in the manner of Example 1.

33.0 g of water-soluble product are obtained, a 5% w/v solution of which has a pH of about 8.3 and which has an Fe$^{II}$ content of 11.0% EXAMPLE 4

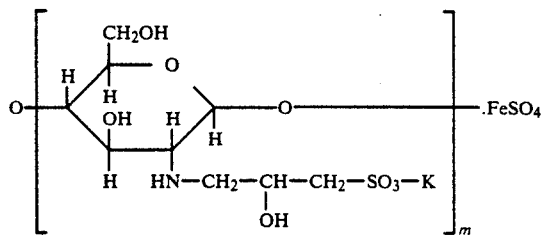

173.9 grams of sodium 3-chloro-2-hydroxy-butyl-sulphonate (0.885 moles) are suspended under stirring in 150 ml of deionized water. 31.8 g (0.800 moles) of solid sodium hydroxide are then added. The mixture is left stirring at 25° C. for 1 hour.

30.0 g (0.177 moles) of chitosan hydrolyzed and activated as described in Example 1 and 450 ml of butanol are then added and the mixture heated under reflux for 8 hours. The cooled suspension is then acidified to pH 3.0 with 1.5N HCl and finally filtered. The solid is washed with methanol/water as described in Example 1. 57.5 g of a water-soluble white solid are obtained with a sodium content <0.2% and an S content of 7.0%.

This solid is dissolved in 600 ml of deionized water. 44.5 g (0.160 moles) of FeSO$_4$.7H$_2$O are added to this solution, which is then left stirring at 25° C. for 16 hours. 70.0 g of product are obtained with an Fe$^{II}$ content of 12%.

The solid is resuspended in 700 ml of deionized water containing 18.0 g of potassium hydroxide (0.32 moles) and the suspension kept stirring for 1 hour at 25° C. By precipitating in the manner described in Example 1, 65.0 g. of water-soluble product are obtained, a 5% w/v solution of which has a pH of 8.4 and which has an Fe$^{II}$ content of 11% and a potassium content of 8.6%.

I claim:

1. Complexes of iron or other metals with sulphonated derivatives of chitosan, having the following formula (I):

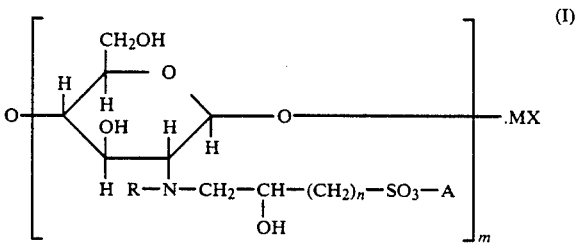

in which:

R is H or a C$_1$–C$_5$ alkyl group, or an arylalkyl group;

A is H or an alkaline metal or an alkaline earth metal;

X is a pharmacologically acceptable anion;

m is a whole number from 50 to 1000;

n is zero or a whole number from 1 to 10;

M is Fe$^{II}$, Fe$^{III}$, Mg, Ca or Bi.

2. Complexes as claimed in claim 1, wherein said anion is sulphate, nitrate, acetate or chloride.

3. A sulphonated derivative of formula (IV):

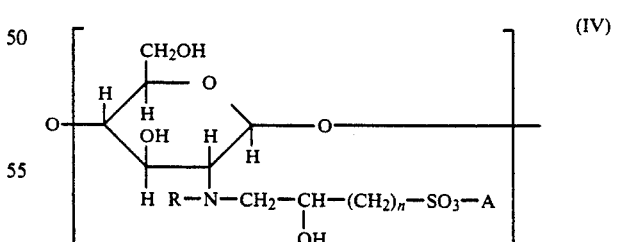

in which:

m is a whole number from 50 to 1000;

R is H or a C$_1$–C$_5$ alkyl group, or an arylalkyl group;

n is zero or a whole number from 1 to 10;

A is H or an alkaline metal or an alkaline earth metal.

4. A process for preparing complexes of iron or other metals with sulphonated derivatives of chitosan, having the following formula (I):

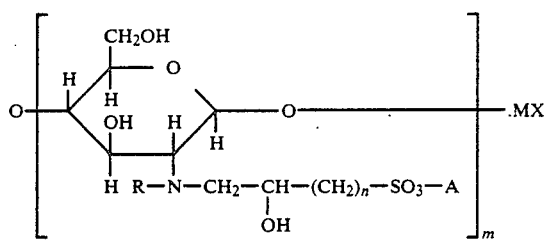

in which:

R is H or a $C_1$–$C_5$ alkyl group, or an arylalkyl group;
A is H or an alkaline metal or an alkaline earth metal;
X is a pharmacologically acceptable anion;
m is a whole number from 50 to 1000;
n is zero or an whole number from 1 to 10;
M is $Fe^{II}$, $Fe^{III}$, Mg, Ca or Bi; consisting of the following steps:
a) hydrolyzing-activating commercial chitosan by treatment with an organic acid, possibly mixed with an alkaline nitrite, and later with alkaline hydroxide;
b) reacting the chitosan obtained in step (a) in an organic solvent or in water or in a mixed organic-aqueous solvent with a chlorohydrin or epoxy compound having the structure (II) and (III):

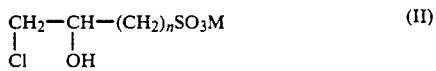

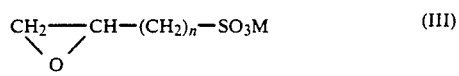

where n is between 0 and 10, and carrying at one end of the chain a sulphonated group where M is hydrogen or an alkaline or alkaline-earth metal;
c) treating with an $Fe^{II}$, $Fe^{III}$, Mg, Ca or Bi salt in aqueous solution and precipitating the complex y adding a water-soluble organic solvent;
d) neutralizing the sulphonic group with an alkaline or alkaline-earth hydroxide or other strong base in aqueous and/or organic or mixed organic/aqueous solution and recovering the neutralized complex by adding a water-soluble organic solvent if operating in water, or by filtration in the remaining cases.

5. A process as claimed in claim 4. wherein said hydrolysis-activation is conducted by treatinG commercial chitosan firstly with 0.1 M acetic or formic acid under reflux for 24 hours and then with 5N NaOH.

6. A process as claimed in claim 4, wherein said hydrolysis-activation is conducted by treating commercial chitosan firstly with 0.4–0.5M acetic acid and sodium nitrite and then with 5N NaOH at ambient temperature.

7. A process as claimed in claim 4, wherein said reacting is conducted in a aqueous medium or in an organic solvent or in a mixed organic/aqueous solvent, said organic solvent being ethylene glycol, methanol or higher homologous alcohols up to 7 carbon atoms. N,Ndimethylformamide, N,N-dimethylacetamide or dimethylsulphoxide.

8. A process as claimed in claim 4, wherein said reacting is conducted with a molar ration of chitosan to chlorohydrin compound or epoxy compound of between 1:0.5 and 1:6 at a temperature of between 60° C. and 120° C. for a time of between 6 and 16 hours.

9. A pharmaceutical composition comprising an aqueous solution containing an effective amount of the compound of formula (I) according to claim 1, wherein M is $Fe^{II}$ or $Fe^{III}$.

* * * * *